(12) United States Patent
Matsuzaki et al.

(10) Patent No.: US 12,059,675 B2
(45) Date of Patent: Aug. 13, 2024

(54) TIP DEVICE, TIP CONTAINER SET, TIP ELECTRODE APPARATUS, AND TIP ELECTRODE SET

(71) Applicant: YOKOGAWA ELECTRIC CORPORATION, Tokyo (JP)

(72) Inventors: Masaaki Matsuzaki, Musashino (JP); Hiroyuki Hosokawa, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 11 days.

(21) Appl. No.: 17/755,759

(22) PCT Filed: Oct. 16, 2020

(86) PCT No.: PCT/JP2020/039180
§ 371 (c)(1),
(2) Date: May 6, 2022

(87) PCT Pub. No.: WO2021/106422
PCT Pub. Date: Jun. 3, 2021

(65) Prior Publication Data
US 2022/0387989 A1 Dec. 8, 2022

(30) Foreign Application Priority Data

Nov. 26, 2019 (JP) .................................. 2019-213560
Apr. 8, 2020 (JP) .................................. 2020-070048

(51) Int. Cl.
*B01L 3/02* (2006.01)
*B01L 3/00* (2006.01)

(52) U.S. Cl.
CPC ........... *B01L 3/0255* (2013.01); *B01L 3/5635* (2013.01)

(58) Field of Classification Search
None
See application file for complete search history.

(56) References Cited

U.S. PATENT DOCUMENTS

| 5,431,280 | A | | 7/1995 | Bryant | |
|---|---|---|---|---|---|
| 5,977,503 | A | * | 11/1999 | Leach | .................... B23H 7/265 |
| | | | | | 219/69.15 |
| 6,448,528 | B1 | * | 9/2002 | Yoshida | .................. B23H 9/14 |
| | | | | | 219/69.15 |
| 2010/0089876 | A1 | * | 4/2010 | Keihl | .................... B23H 7/265 |
| | | | | | 219/69.15 |

(Continued)

FOREIGN PATENT DOCUMENTS

| JP | 62-179084 U | 11/1987 |
|---|---|---|
| JP | 11-295282 A | 10/1999 |

(Continued)

OTHER PUBLICATIONS

Partial Supplementary European Search Report dated Mar. 4, 2024 issued in European patent application No. 20893903.3.

(Continued)

*Primary Examiner* — P. Kathryn Wright
(74) *Attorney, Agent, or Firm* — RANKIN, HILL & CLARK LLP

(57) ABSTRACT

A tip device (1) includes a tubular tip (6) and a base (8) that is continuous with a rear end (6a) of the tip (6) and includes a first connector. The first connector detachably connects to a second connector provided in a container (2) to house the tip (6).

19 Claims, 13 Drawing Sheets

(56) References Cited

U.S. PATENT DOCUMENTS

2011/0300621 A1    12/2011  Belz et al.
2022/0257156 A1*   8/2022  Iwasawa .......... A61B 5/150351

FOREIGN PATENT DOCUMENTS

| JP | 2002-542017 A | 12/2002 |
|----|---------------|---------|
| JP | 2008-509709 A | 4/2008 |
| JP | 5317983 B2 | 10/2013 |
| JP | 2014530358 A | 11/2014 |
| JP | 6090387 B2 | 3/2017 |
| JP | 2018-143999 A | 9/2018 |
| JP | 6444560 B1 | 12/2018 |
| JP | 2019-33680 A | 3/2019 |
| WO | 03/057819 A1 | 7/2003 |
| WO | 2013052318 A1 | 4/2013 |

OTHER PUBLICATIONS

Extended European Search Report dated May 29, 2024 issued in European patent application No. 20893903.3.

* cited by examiner

TIP DEVICE, TIP CONTAINER SET, TIP ELECTRODE APPARATUS, AND TIP ELECTRODE SET

CROSS-REFERENCE TO RELATED APPLICATIONS

The present application claims priority to Japanese Patent Application No. 2019-213560 filed on Nov. 26, 2019, and Japanese Patent Application No. 2020-70048 filed on Apr. 8, 2020, the entire contents of which are incorporated herein by reference.

TECHNICAL FIELD

The present disclosure relates to a tip device, a tip container set, a tip electrode apparatus, and a tip electrode set.

BACKGROUND

Tubular tips, such as those described in patent literature (PTL) 1 to 4, are known.

CITATION LIST

Patent Literature

PTL 1: JP 5317983 B2
PTL 2: JP 6090387 B2
PTL 3: JP 2019-33680 A
PTL 4: JP H11-295282 A

SUMMARY

Technical Problem

Such tips may be used as follows for purposes such as measurement, injection, or collection of cells or other such samples. First, liquid is introduced from the rear end of the tip. Next, the tip is held in a container that houses the tip. The container is then centrifuged so that the head of the tip is filled with liquid without a gap, i.e., without air bubbles. The tip is then removed from the container, and a microscope is used to confirm that the head of the tip is filled with liquid without a gap. If the head is not filled with liquid without a gap, the tip is centrifuged again. Once it is confirmed that the head is filled with liquid without a gap, a wire electrode is introduced from the rear end of the tip, and the rear end of the tip is held in an electrode holder. This enables the tip of the electrode to be immersed in the liquid inside the head of the tip. The head of the tip is then immersed in the sample, and an electric field is applied between the sample and the electrode to achieve the various purposes described above.

Conventional tips cannot, however, be easily inserted into or removed from the container or the electrode holder.

Therefore, the present disclosure aims to provide a tip device that enables a tip to be easily inserted into and removed from a container, a tip device that enables a tip to be easily inserted into and removed from an electrode holder, a tip container set that enables a tip to be easily inserted into and removed from a container, a tip electrode apparatus that enables a tip to be easily inserted into and removed from an electrode holder, and a tip electrode set that enables a tip to be easily inserted into and removed from an electrode holder.

Solution to Problem

A tip device according to an embodiment includes a tubular tip; and a base that is continuous with a rear end of the tip and includes a first connector, wherein the first connector detachably connects to a second connector provided in a container to house the tip. According to this configuration, the tip can easily be inserted into and removed from the container via the base.

A tip device according to an embodiment includes a tubular tip; and a base that is continuous with a rear end of the tip and includes a first connector, wherein the first connector detachably connects to a second connector provided in an electrode holder, and a linear electrode to be introduced into the rear end of the tip protrudes from the electrode holder. According to this configuration, the tip can easily be inserted into and removed from the electrode holder via the base.

In a tip device according to an embodiment, the base may be located between the first connector and a head of the tip and include a grip that is wider in a radial direction of the tip. According to this configuration, the tip can easily be inserted into and removed from the container or the electrode holder by use of the grip.

In a tip device according to an embodiment, the base may include an access hole that communicates with the rear end of the tip. According to this configuration, a liquid or an electrode can easily be introduced into the rear end of the tip via the access hole.

In a tip device according to an embodiment, the access hole may include a guide face that gradually narrows in diameter towards the rear end of the tip. According to this configuration, a liquid or an electrode can more easily be introduced into the rear end of the tip by the guide face.

In a tip device according to an embodiment, the base may include a grounding portion configured to maintain a head of the tip separated from a flat surface on which the tip is placed. According to this configuration, contamination of the head of the tip can be easily controlled when the tip is placed down.

In a tip device according to an embodiment, the grounding portion may be located on an outer peripheral surface of the base. According to this configuration, contamination of the head of the tip can be easily controlled when the head of the tip is observed under a microscope.

In a tip device according to an embodiment, the connectors may connect by concavo-convex engagement with each other.

According to this configuration, the tip can be held more reliably by the container or the electrode holder.

In a tip device according to an embodiment, the connectors may connect by screwing together. According to this configuration, the tip can be held even more reliably by the container or the electrode holder.

In a tip device according to an embodiment, the head may be formed as a nano-tip having a nanometer-order inner diameter. According to this configuration, measurement, injection, collection, or the like can easily be performed on a minute portion of a sample, such as an intracellular organ, using the tip device.

A tip container set according to an embodiment includes a tubular tip; a base that is continuous with a rear end of the tip and includes a first connector; and a container configured to house the tip and including a second connector that detachably connects to the first connector. According to this configuration, the tip can easily be inserted into and removed from the container via the base.

In a tip container set according to an embodiment, the container may include a communication hole through which an exterior of the container communicates with the rear end of the tip. According to this configuration, liquid can be introduced through the communication hole from the rear end of the tip while the tip is housed in the container, and the tip can be centrifuged as is, thereby streamlining the work of filling the head of the tip with liquid.

In a tip container set according to an embodiment, the container may include a cap and a container body, the cap including the second connector, and the container body including an opening that detachably connects to the cap. According to this configuration, the container can be configured by a simple structure.

In a tip container set according to an embodiment, the base may be located between the first connector and a head of the tip and include a grip that is wider in a radial direction of the tip. According to this configuration, the tip can easily be inserted into and removed from the container by use of the grip.

In a tip container set according to an embodiment, the base may include an access hole that communicates with the rear end of the tip. According to this configuration, a liquid or an electrode can easily be introduced into the rear end of the tip via the access hole.

In a tip container set according to an embodiment, the access hole may include a guide face that gradually narrows in diameter towards the rear end of the tip. According to this configuration, a liquid or an electrode can more easily be introduced into the rear end of the tip by the guide face.

In a tip container set according to an embodiment, the base may include a grounding portion configured to maintain a head of the tip separated from a flat surface on which the tip is placed. According to this configuration, contamination of the head of the tip can be easily controlled when the tip is placed down.

In a tip container set according to an embodiment, the grounding portion may be located on an outer peripheral surface of the base. According to this configuration, contamination of the head of the tip can be easily controlled when the head of the tip is observed under a microscope.

In a tip container set according to an embodiment, the connectors may connect by concavo-convex engagement with each other. According to this configuration, the tip can be held more reliably by the container.

In a tip container set according to an embodiment, the connectors may connect by screwing together. According to this configuration, the tip can be held even more reliably by the container.

In a tip container set according to an embodiment, the head of a tip device may be formed as a nano-tip having a nanometer-order inner diameter. According to this configuration, measurement, injection, collection, or the like can easily be performed on a minute portion of a sample, such as an intracellular organ, using the tip device.

A tip electrode apparatus according to an embodiment includes a tubular tip; a base that is continuous with a rear end of the tip and includes a first connector; an electrode holder including a second connector that detachably connects to the first connector; and a linear electrode that protrudes from the electrode holder and is introduced into the rear end of the tip. According to this configuration, the tip can easily be inserted into and removed from the electrode holder via the base.

In a tip electrode apparatus according to an embodiment, the base may be located between the first connector and a head of the tip and include a grip that is wider in a radial direction of the tip. According to this configuration, the tip can easily be inserted into and removed from the electrode holder by use of the grip.

In a tip electrode apparatus according to an embodiment, the base may include an access hole that communicates with the rear end of the tip. According to this configuration, a liquid or an electrode can easily be introduced into the rear end of the tip via the access hole.

In a tip electrode apparatus according to an embodiment, the access hole may include a guide face that gradually narrows in diameter towards the rear end of the tip. According to this configuration, a liquid or an electrode can more easily be introduced into the rear end of the tip by the guide face.

In a tip electrode apparatus according to an embodiment, the base may include a grounding portion configured to maintain a head of the tip separated from a flat surface on which the tip is placed. According to this configuration, contamination of the head of the tip can be easily controlled when the tip is placed down.

In a tip electrode apparatus according to an embodiment, the grounding portion may be located on an outer peripheral surface of the base. According to this configuration, contamination of the head of the tip can be easily controlled when the head of the tip is observed under a microscope.

In a tip electrode apparatus according to an embodiment, the connectors may connect by concavo-convex engagement with each other. According to this configuration, the tip can be held more reliably by the electrode holder.

In a tip electrode apparatus according to an embodiment, the connectors may connect by screwing together. According to this configuration, the tip can be held even more reliably by the electrode holder.

In a tip electrode apparatus according to an embodiment, the head of a tip device may be formed as a nano-tip having a nanometer-order inner diameter. According to this configuration, measurement, injection, collection, or the like can easily be performed on a minute portion of a sample, such as an intracellular organ, using the tip device.

In a tip electrode apparatus according to an embodiment, the electrode holder may include a first terminal continuous with a rear end of the electrode and a second terminal that detachably contacts the first terminal. According to this configuration, when the tip device held in the electrode holder is replaced, an electrode device that includes the electrode and the first terminal can also be replaced. Therefore, liquid that was attached to the electrode before replacement of the tip device can be prevented from mixing with the liquid in the tip device after the replacement.

A tip electrode set according to an embodiment includes: a tubular tip; a base that is continuous with a rear end of the tip and includes a first connector; and an electrode device including a linear electrode introduced into the rear end of the tip and a first terminal continuous with a rear end of the electrode, wherein the first connector detachably connects to a second connector provided in an electrode holder, and the first terminal detachably contacts a second terminal provided in the electrode holder. According to this configuration, the tip can easily be inserted into and removed from the electrode holder via the base. Furthermore, according to this configuration, when the tip device held in the electrode holder is replaced, the electrode device can also be replaced. Therefore, liquid that was attached to the electrode before replacement of the tip device can be prevented from mixing with the liquid in the tip device after the replacement.

Advantageous Effect

According to the present disclosure, a tip device that enables a tip to be easily inserted into and removed from a container, a tip device that enables a tip to be easily inserted into and removed from an electrode holder, a tip container set that enables a tip to be easily inserted into and removed from a container, a tip electrode apparatus that enables a tip to be easily inserted into and removed from an electrode holder, and a tip electrode set that enables a tip to be easily inserted into and removed from an electrode holder can be provided.

DETAILED DESCRIPTION

Embodiments of the present disclosure are described below with reference to the drawings.

Figure 1:
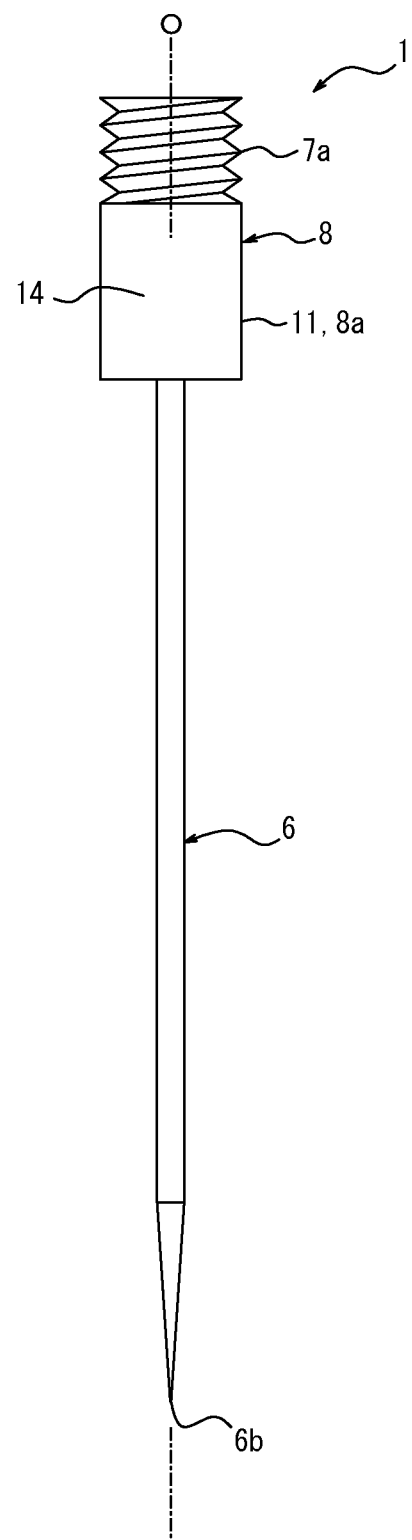
FIG. 1 is a side view illustrating a tip device according to an embodiment.
Figure 2:
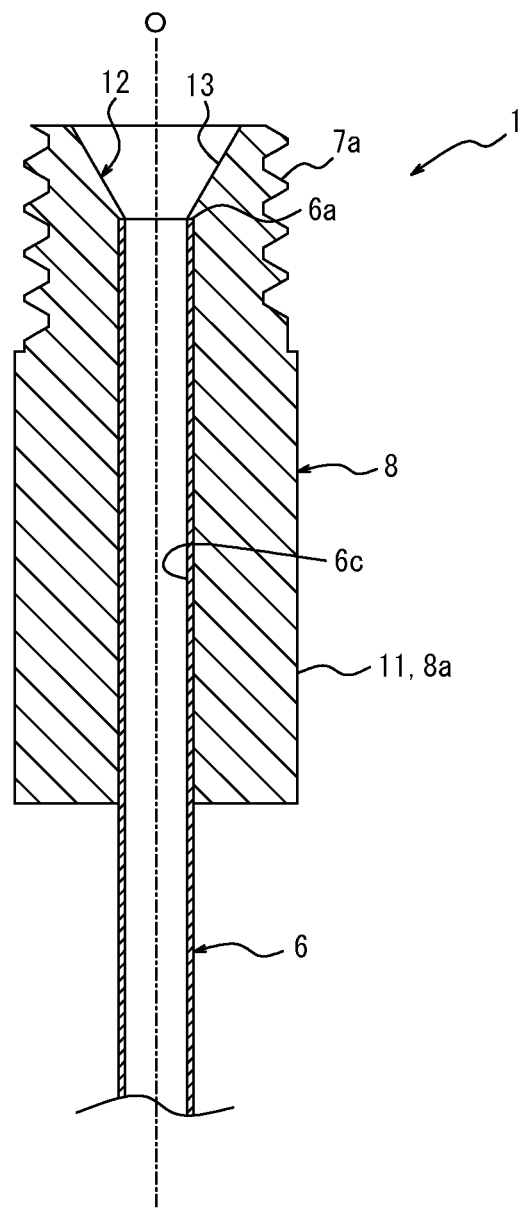
FIG. 2 is a cross-sectional view of the tip device illustrated in FIG. 1.
Figure 3:
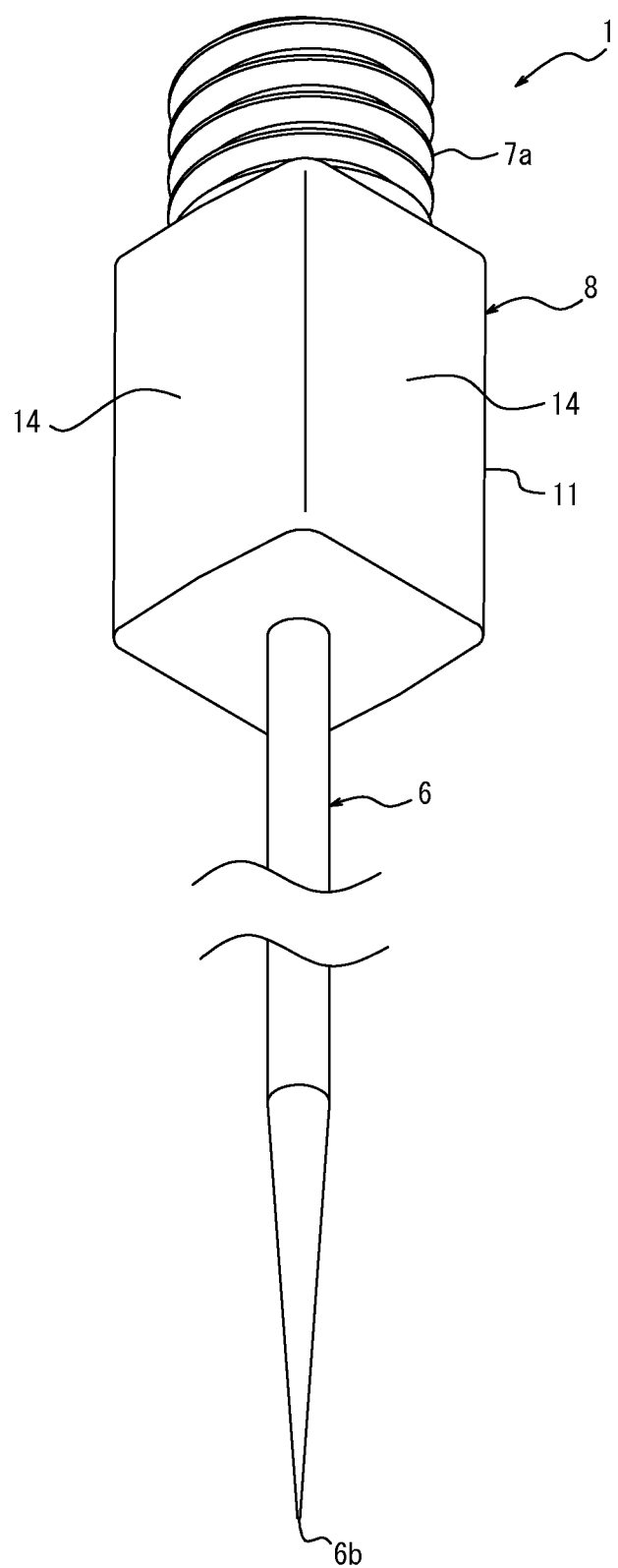
FIG. 3 is a perspective view of the tip device illustrated in FIG. 1.
Figure 4:
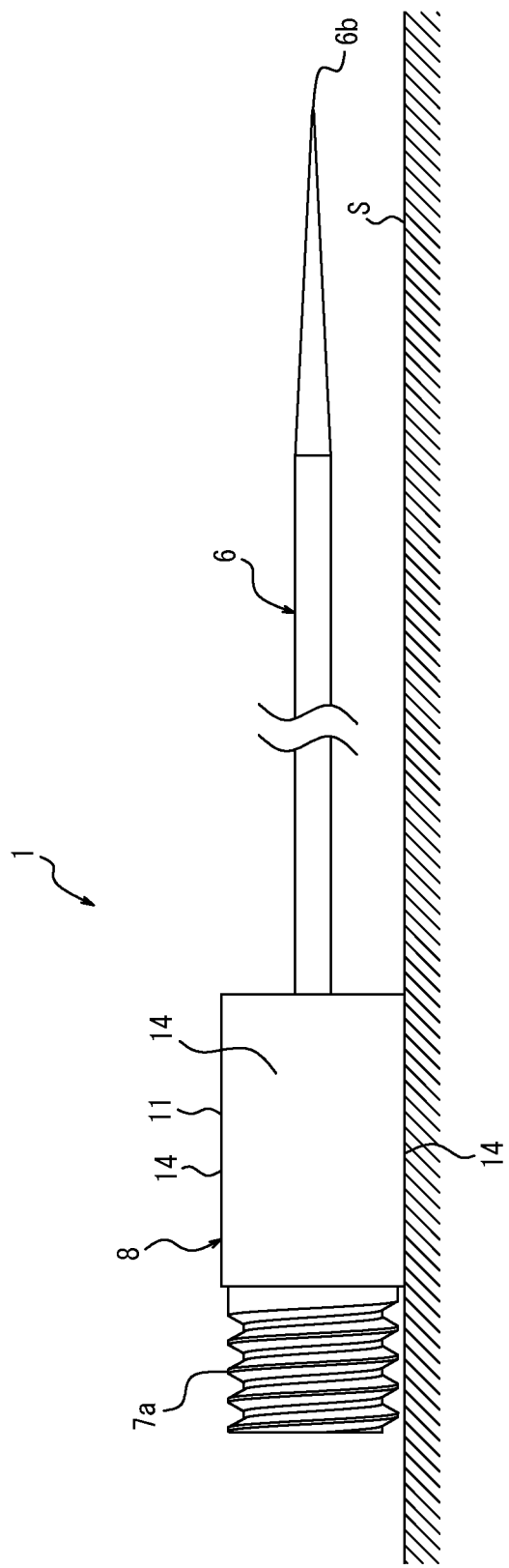
FIG. 4 is a side view illustrating the tip device in FIG. 1 once the tip device has been placed down.
Figure 5:
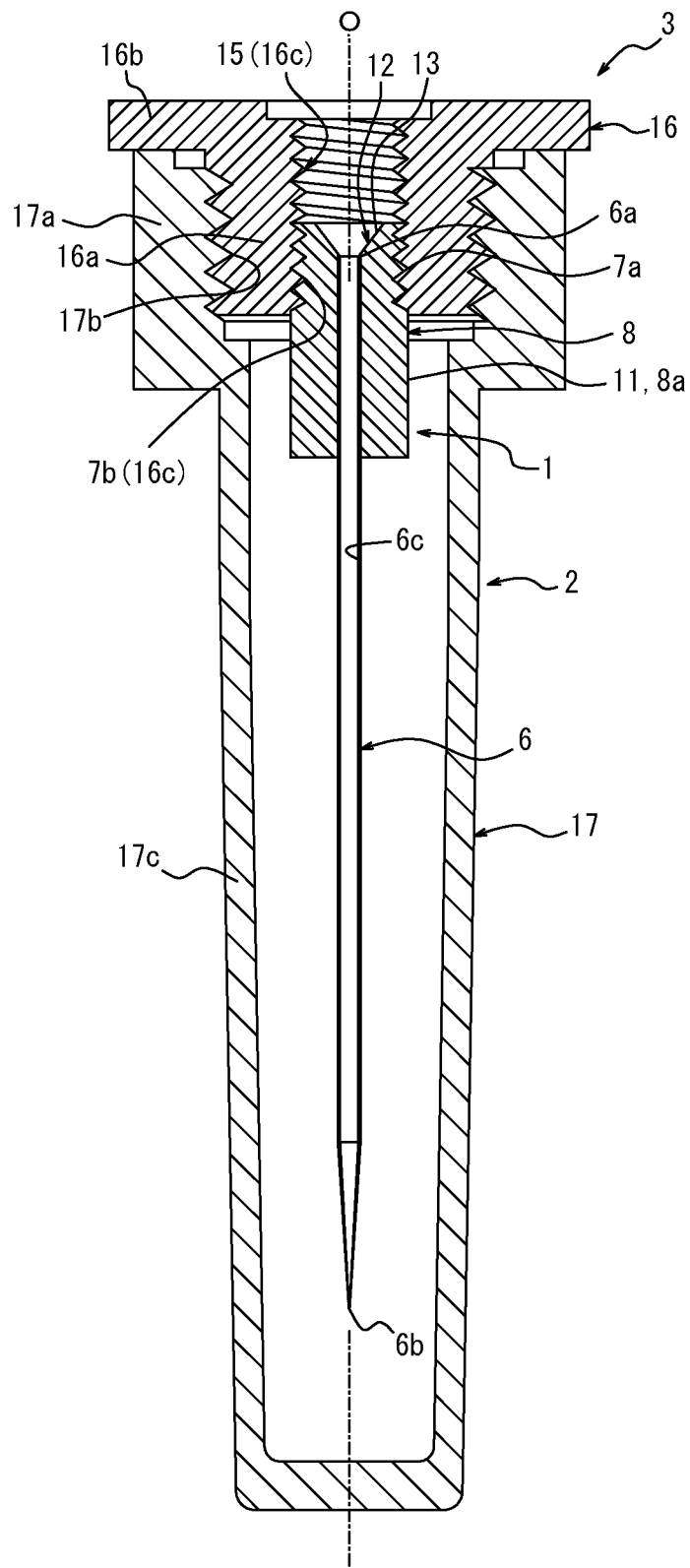
FIG. 5 is a cross-sectional view illustrating a tip container set according to an embodiment.
Figure 6:
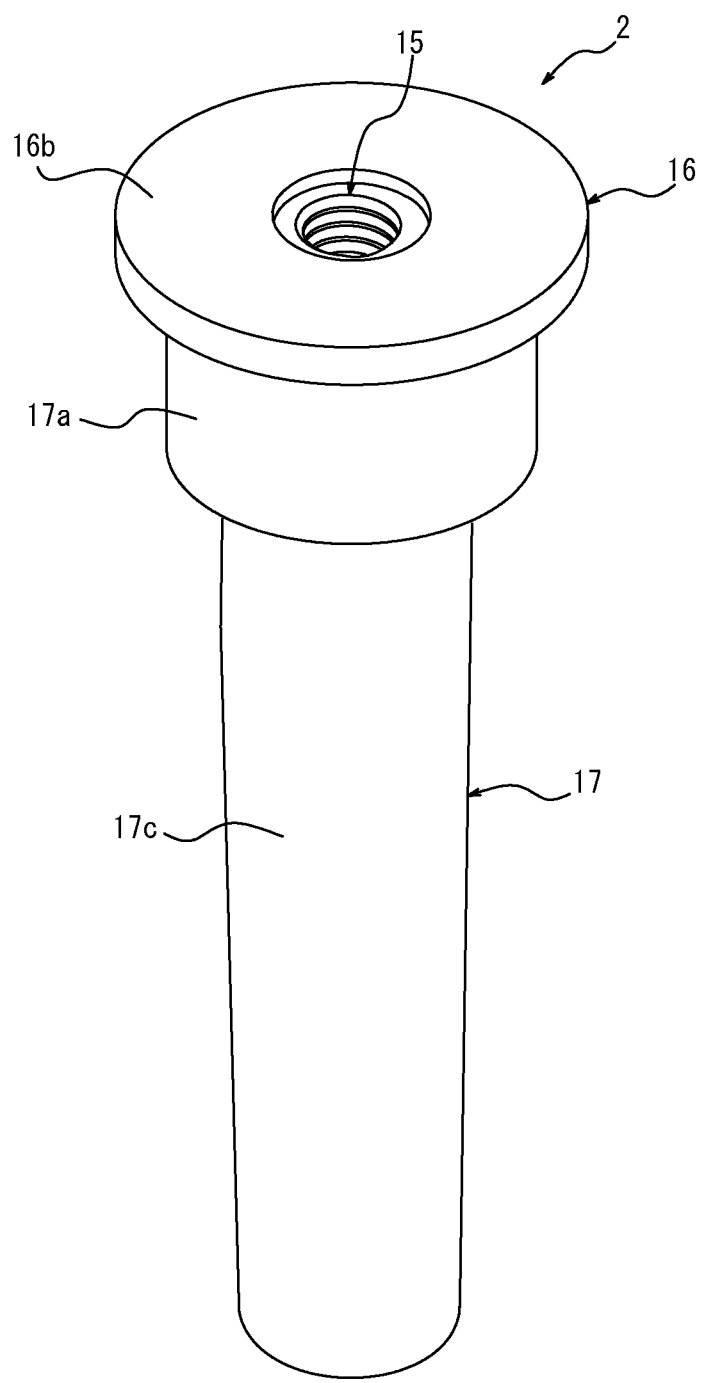
FIG. 6 is a perspective view illustrating the container in FIG. 5 with a cap closed.
Figure 7:
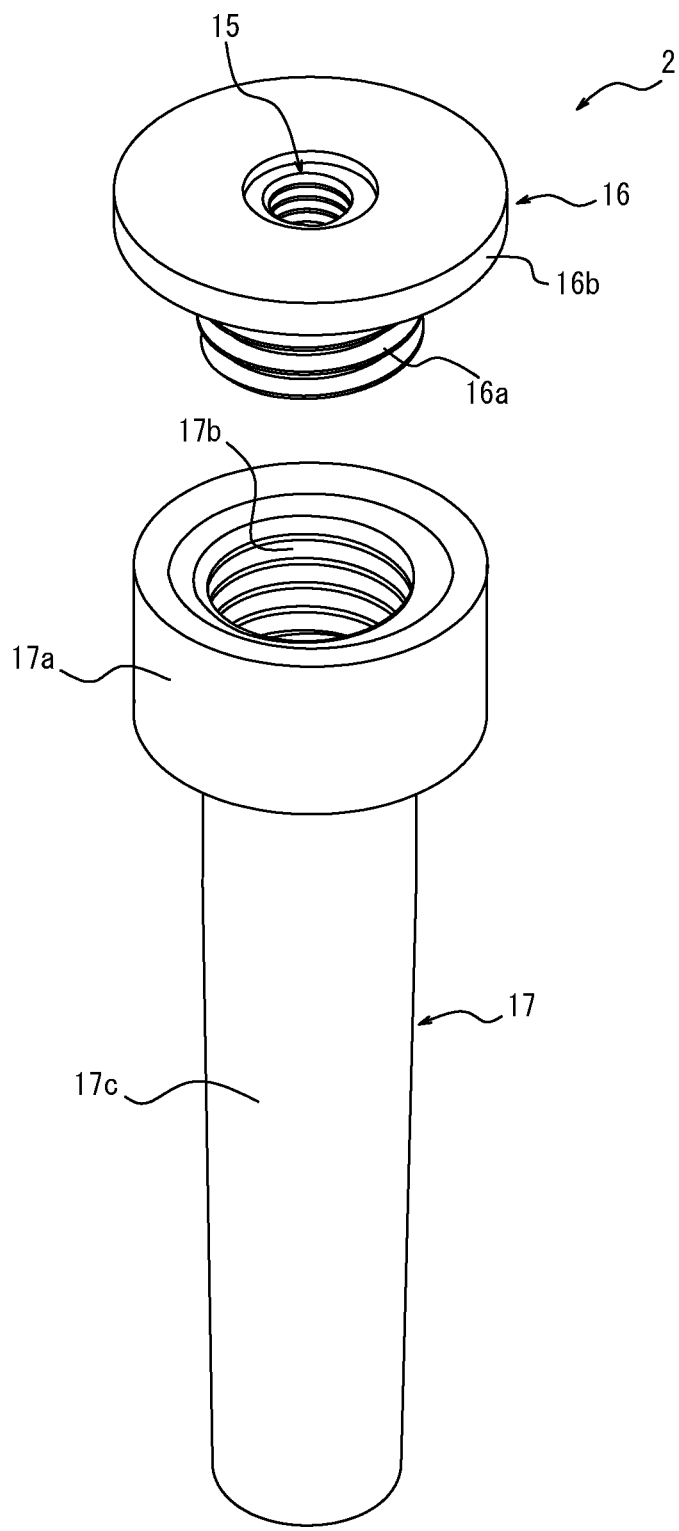
FIG. 7 is a perspective view illustrating the container in FIG. 5 with the cap open.
Figure 8:
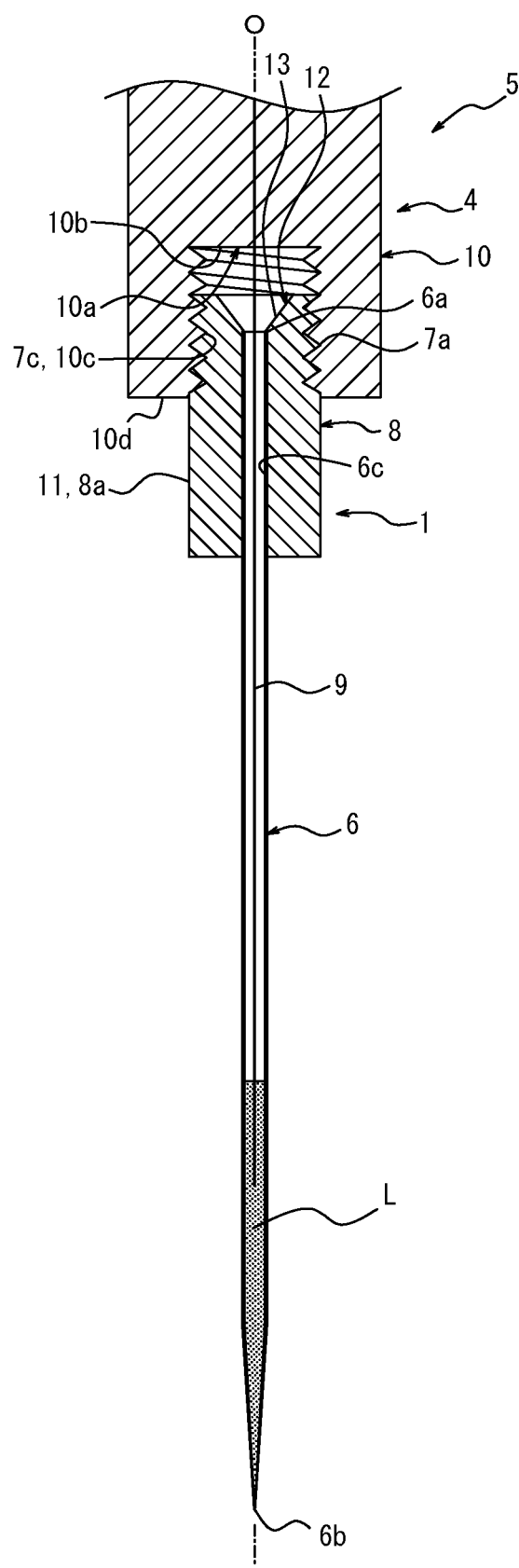
FIG. 8 is a cross-sectional view illustrating a tip electrode apparatus according to an embodiment.
Figure 9:
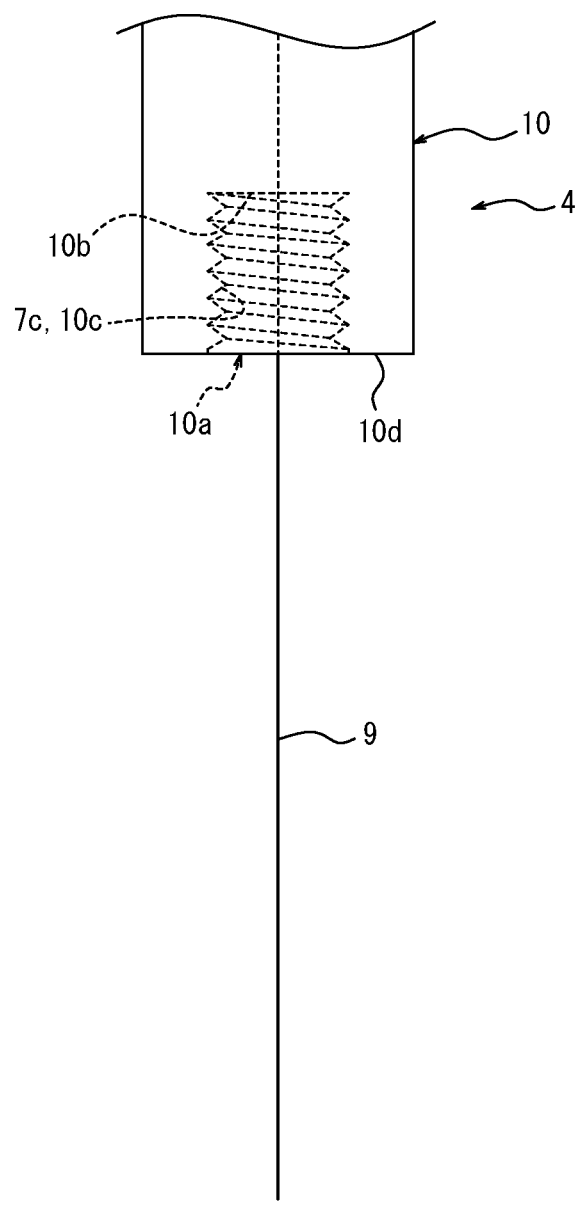
FIG. 9 is a side view of the electrode apparatus illustrated in FIG. 8.

In an embodiment, the tip device 1 illustrated in FIGS. 1 to 4 forms a tip container set 3 by being combined with the container 2, illustrated in FIGS. 5 to 7, that houses the tip device 1, and forms a tip electrode apparatus 5 by being combined with the electrode apparatus 4 illustrated in FIGS. 8 and 9. The applications of the tip device 1 are not, however, limited to use in combination with the container 2 and the electrode apparatus 4.

As illustrated in FIGS. 1 to 4, the tip device 1 includes a tubular tip 6 and a base 8 that is continuous with a rear end 6a of the tip 6 and that includes a base connector 7a as a first connector. The base connector 7a detachably connects to a container connector 7b as a second connector provided in the container 2 to house the tip 6. The base connector 7a detachably connects to a holder connector 7c as a second connector provided in an electrode holder 10. A linear electrode 9 to be introduced into the rear end 6a of the tip 6 protrudes from the electrode holder 10.

The tip 6 is formed as a nano-tip with a head 6b having a nanometer-order inner diameter, but this configuration is not limiting. The head 6b of the tip 6 has an inner diameter of 100 nm, for example. The tip 6 is cylindrical, centered on an axial center O, with the head 6b gradually decreasing in diameter towards the end, but this configuration is not limiting. The tip 6 is, for example, formed of glass.

The base 8 is made of synthetic resin, for example, and is adhered to the rear end 6a of the tip 6 by appropriate means, for example. Example of means for adhering include adhesion, friction-based engagement, concavo-convex engagement, welding, and insert molding.

The base 8 is a square cylinder centered on the axial center O, but this configuration is not limiting. The base 8 is provided so as to protrude farther towards the rear end than the rear end 6a of the tip 6, but this configuration is not limiting.

The base 8 is located between the base connector 7a and the head 6b of the tip 6 and includes a grip 11 that is wider in the radial direction of the tip 6, but this configuration is not limiting.

The base 8 includes an access hole 12 that communicates with the rear end 6a of the tip 6, but this configuration is not limiting. The access hole 12 includes a guide face 13 that gradually narrows in diameter towards the rear end 6a of the tip 6, but this configuration is not limiting. The guide face 13 is conical, but this configuration is not limiting. The front edge of the guide face 13 coincides with the back edge of an inner peripheral surface 6c of the tip 6, but this configuration is not limiting.

The base 8 includes a grounding portion 14 configured to maintain the head 6b of the tip 6 separated from a flat surface S on which the tip 6 is placed, but this configuration is not limiting. The grounding portion 14 is located on the outer peripheral surface 8a of the base 8, but this configuration is not limiting. The base 8 is a rectangular column including the outer peripheral surface 8a, which has four flat faces that can each serve as the grounding portion 14, but this configuration is not limiting. The grounding portion 14 is not limited to being a flat surface but can also be curved, for example. The center of gravity of the base 8 can be appropriately set so that when the grounding portion 14 is placed in contact with the surface S, the head 6b of the tip 6 is kept separated from the surface S.

The base connector 7a and the container connector 7b or holder connector 7c are configured to be connected by concavo-convex engagement, but this configuration is not limiting. For example, these connectors may be configured to be connected by friction-based engagement. The base connector 7a and the container connector 7b or holder connector 7c are configured to be connected by screwing, but this configuration is not limiting. For example, these connectors may be configured to be connected by concavo-convex engagement other than screwing.

As illustrated in FIGS. 5 to 7, the container 2 includes a communication hole 15 through which the exterior of the container 2 communicates with the rear end 6a of the tip 6, but this configuration is not limiting. The communication hole 15 is concentric with the axial center O of the tip 6, but this configuration is not limiting.

The container 2 includes a cap 16, which includes the container connector 7b, and a container body 17 including an opening 17a that detachably connects to the cap 16, but this configuration is not limiting. The container 2 is, for example, formed from synthetic resin.

The cap 16 includes a cylindrical tube wall 16a centered on the axial center O and an annular flange 16b extending radially outward from the upper end of the tube wall 16a, but this configuration is not limiting. The lower end of the inner peripheral surface 16c of the tube wall 16a forms the container connector 7b. The remainder of the inner peripheral surface 16c of the tube wall 16a forms the communication hole 15. The tube wall 16a is cylindrical, but this configuration is not limiting, and the tube wall 16a may be a non-cylindrical tube. The flange 16b is circular, but this configuration is not limiting, and the flange 16b may be a non-circular ring.

In the present specification, the up-down direction refers to the direction along the axial center O, upward refers to the direction from the head 6b of the tip 6 to the rear end 6a of the tip 6 (i.e., upward in FIGS. 5 and 10), and downward refers to the opposite direction.

The outer peripheral surface of the tube wall 16a detachably connects to the inner peripheral surface 17b of the opening 17a, but this configuration is not limiting. The outer peripheral surface of the tube wall 16a is configured to be connected by concavo-convex engagement to the inner peripheral surface 17b of the opening 17a, but this configuration is not limiting. For example, these surfaces may be configured to be connected by friction-based engagement. The outer peripheral surface of the tube wall 16a is configured to be connected by screwing to the inner peripheral surface 17b of the opening 17a, but this configuration is not limiting. For example, these surfaces may be configured to be connected by concavo-convex engagement other than screwing.

The opening 17a of the container body 17 is cylindrical, but this configuration is not limiting, and the opening 17a may be a non-cylindrical tube. A torso 17c that surrounds the tip device 1 is connected to the opening 17a. The torso 17c has a bottomed cylindrical shape extending downward from the lower end of the opening 17a, but this configuration is not limiting. For example, the shape of the torso 17c is not limited to a bottomed cylindrical shape. The torso 17c has a bottomed cylindrical shape, but this configuration is not limiting, and the torso 17c may have a bottomed tubular shape other than a bottomed cylindrical shape.

As illustrated in FIGS. 8 and 9, the tip electrode apparatus 5 includes the tip device 1 and the electrode apparatus 4. The electrode apparatus 4 includes the electrode holder 10, which includes the holder connector 7c, and the linear electrode 9 that protrudes from the electrode holder 10 and is introduced into the rear end 6a of the tip 6. The electrode 9 is, for example, formed from a metal such as silver. The electrode holder 10 is, for example, formed from synthetic resin.

The electrode holder 10 includes a downward opening recess 10a concentric with the axial center O of the tip 6, but this configuration is not limiting. The electrode 9 protrudes downward from an upper end face 10b of the recess 10a concentrically with the axial center O, but this configuration is not limiting. The holder connector 7c is configured by an inner peripheral surface 10c of the recess 10a, but this configuration is not limiting. The electrode 9 extends to the head-side portion of the tip 6 with the base connector 7a and the holder connector 7c in a connected state, but this configuration is not limiting. The tip 6 is filled with a liquid L, and the head 9a of the electrode 9 is immersed in the liquid L. The liquid L fills the head 6b of the tip 6 without any gaps, i.e., without any air bubbles. The amount of liquid L and the length of the electrode 9 can be changed as needed.

The recess 10a is formed in the head 10d of the electrode holder 10, but this configuration is not limiting. The head 10d of the electrode holder 10 is cylindrical, but this configuration is not limiting, and the head 10d may be a non-cylindrical tube.

In the present embodiment, the tip device 1 is used as follows for purposes such as measurement, injection, or collection of cells or other such samples, but this configuration is not limiting.

First, the tip device 1 is distributed, sold, and stored while housed in the container 2, as illustrated in FIG. 5. Then, at the time of use, the liquid L is introduced from the rear end 6a of the tip 6 using a pipette, for example, while the tip device 1 remains in this state. That is, by insertion of the pipette into the rear end 6a of the tip 6 through the communication hole 15 and the access hole 12, the liquid L is introduced into the tip 6. At this time, the pipette can be guided into the rear end 6a of the tip 6 by the guide face 13 of the access hole 12. Upon introduction of the liquid L, the tip container set 3 is centrifuged.

After the process with the centrifuge is complete, the cap 16 of the container 2 is opened, and the tip device 1 is removed from the cap 16. The removed tip device 1 is placed on the surface S via the grounding portion 14, as illustrated in FIG. 4, and the head 6b of the tip 6 is observed under a microscope. At this time, the head 6b of the tip 6 is kept separated from the surface S, so that contamination of the head 6b of the tip 6 can be easily controlled. In a case in which the liquid L does not fill the head 6b without gaps, the tip device 1 is again attached to the cap 16, the cap 16 is closed, and the tip container set 3 is placed back in the centrifuge.

In this way, the tip device 1 can easily be inserted into and removed from the container 2 via the base connector 7a and the container connector 7b. Furthermore, the operation to insert and remove the tip device 1 into and from the container 2 can be performed easily by gripping the grip 11 with a finger, for example.

Once this observation confirms that the liquid L has filled the head 6b of the tip 6 without gaps, the tip device 1 is attached to the electrode apparatus 4 as illustrated in FIG. 8. That is, the electrode 9 is inserted into the rear end 6a of the tip 6 through the access hole 12, and the tip device 1 is attached to the electrode holder 10 via the base connector 7a and the holder connector 7c. At this time, the electrode 9 can be guided into the rear end 6a of the tip 6 by the guide face 13 of the access hole 12. The head 6b of the tip 6 is then immersed in a sample, and an electric field is applied between the sample and the electrode 9 to achieve the various purposes described above.

In this way, the tip device 1 can easily be inserted into and removed from the electrode apparatus 4 via the base connector 7a and the holder connector 7c. Furthermore, the operation to insert and remove the tip device 1 into and from the electrode apparatus 4 can be performed easily by gripping the grip 11 with a finger, for example.

According to the tip device 1 of the present embodiment, not only can the operation of inserting and removing the tip 6 into and from the container 2 and electrode holder 10 be completed quickly, but also the occurrence of tip damage due to mishandling at the time of insertion and removal, and the resulting need for repeated operations, can be reduced. Accordingly, the efficiency of a series of operations for achieving the various objectives described above can be dramatically increased.

Figure 10:
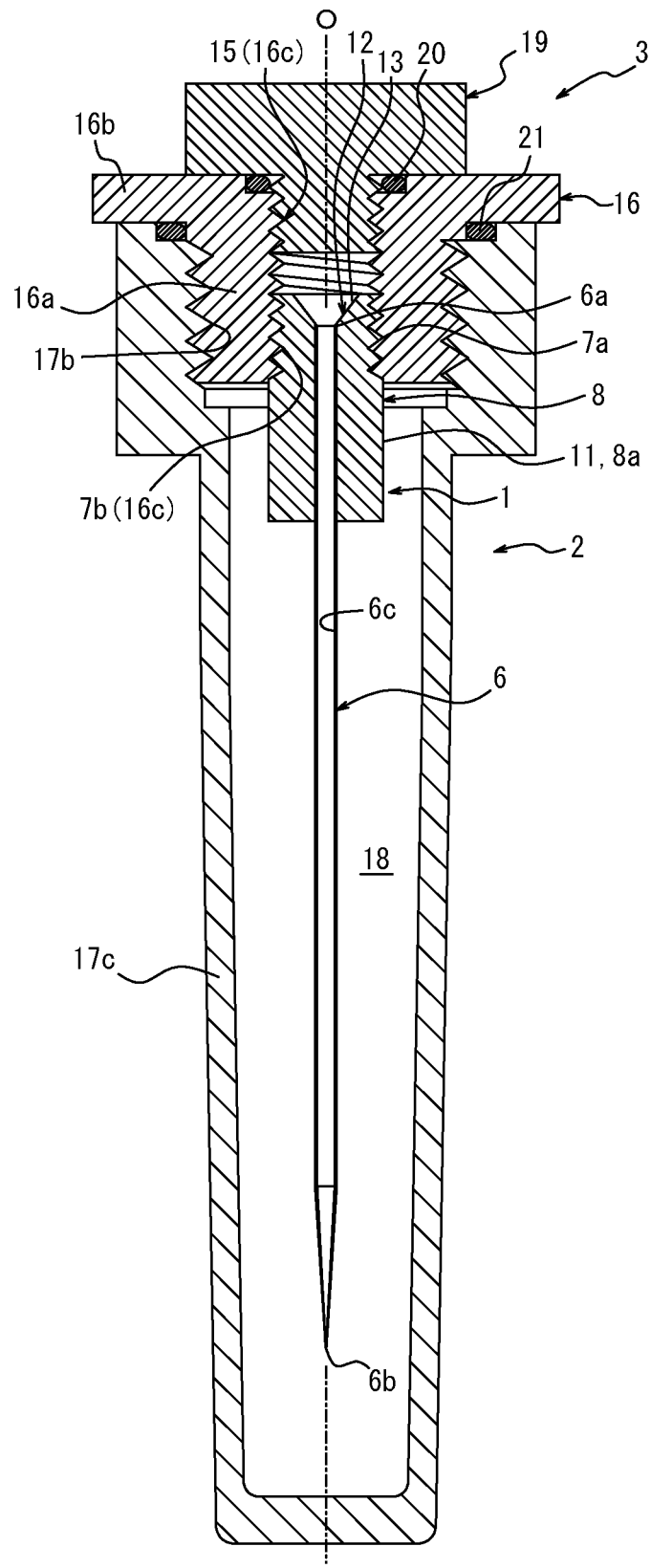
FIG. 10 is a cross-sectional view illustrating a tip container set according to another embodiment.
Figure 11:
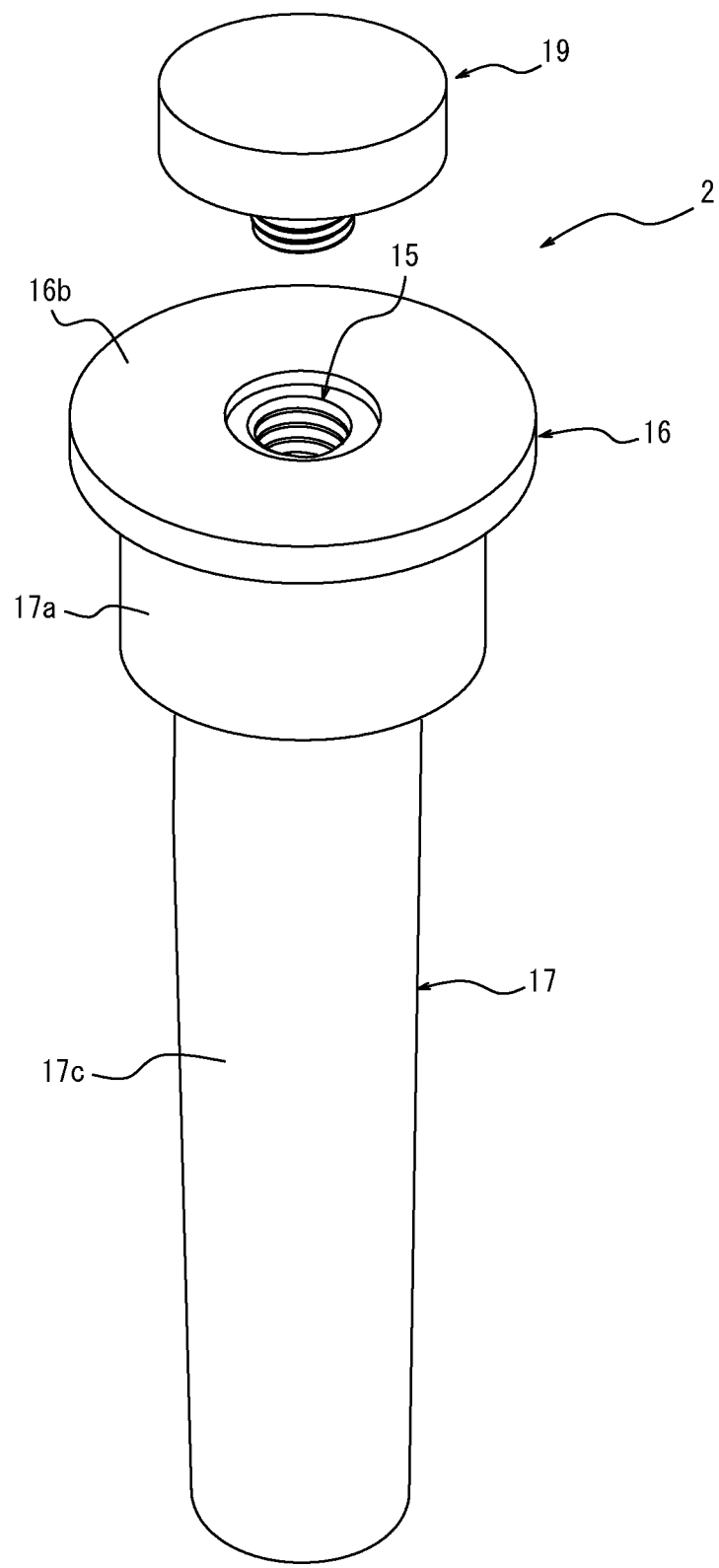
FIG. 11 is a perspective view illustrating the container in FIG. 10 with a blocking cap open while a cap is closed.

The tip device 1 according to the embodiment described above can also be combined with the container 2 according to another embodiment illustrated in FIGS. 10 and 11 to configure the tip container set 3 according to another embodiment. In FIGS. 10 and 11, elements corresponding to those in the embodiment described above are labeled with the same reference signs.

In the present embodiment, the container 2 is configured to form a sealed space 18 that houses the tip device 1. To this end, the container 2 further includes a blocking cap 19 that openably blocks the communication hole 15 of the cap 16. The blocking cap 19 is configured to be connected by concavo-convex engagement to the communication hole 15, but this configuration is not limiting. For example, these components may be configured to be connected by friction-based engagement. The blocking cap 19 is configured to be connected by screwing to the communication hole 15, but this configuration is not limiting. For example, these components may be configured to be connected by concavo-convex engagement other than screwing.

An annular first sealing member 20 is further provided between the communication hole 15 and the blocking cap 19, but this configuration is not limiting. The first sealing member 20 is held by the blocking cap 19, but this configuration is not limiting. The first sealing member 20 may be held by the cap 16. An annular second sealing member 21 is further provided between the cap 16 and the opening 17a, but this configuration is not limiting. The second sealing member 21 may be held by either the cap 16 or the opening 17a.

The tip container set 3 is distributed, sold, and stored, for example, while housing the tip device 1 and with the container 2 filled with a desired fluid, such as the liquid L. The tip container set 3 can, for example, also be used for the same purposes and in the same manner as in the embodiments described above by removing the blocking cap 19 from the cap 16.

Figure 12:
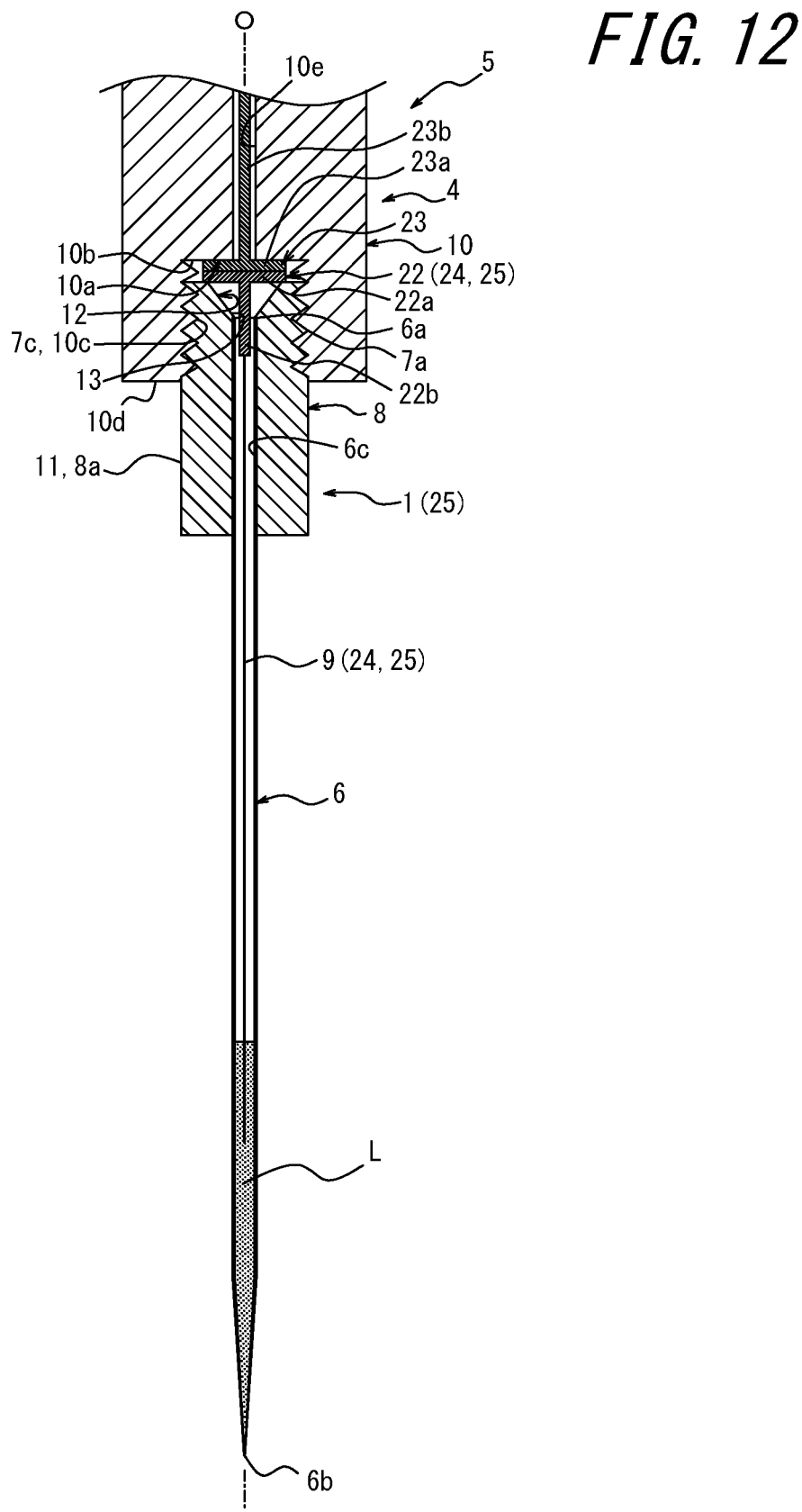
FIG. 12 is a cross-sectional view illustrating a tip electrode apparatus according to another embodiment, with an electrode terminal and a holder terminal in contact with each other.
Figure 13:
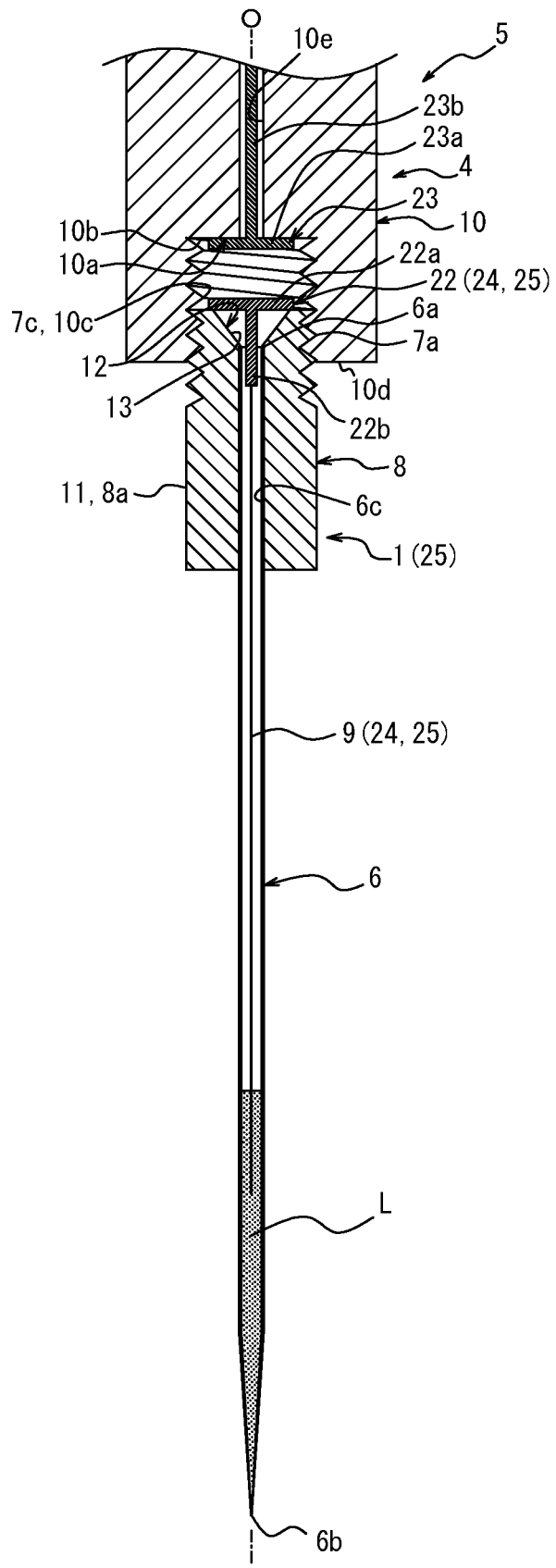
FIG. 13 is a cross-sectional view illustrating the tip electrode apparatus in FIG. 12, with the electrode terminal and the holder terminal separated from each other.

The tip device 1 according to the embodiment described above can also be combined with the electrode apparatus 4 according to another embodiment illustrated in FIGS. 12 and 13 to configure the tip electrode apparatus 5 according to another embodiment. In FIGS. 12 and 13, elements corresponding to those in the embodiment described above are labeled with the same reference signs.

In the present embodiment, the electrode holder 10 includes an electrode terminal 22 as a first terminal continuous with the rear end of the electrode 9 and a holder terminal 23 as a second terminal that detachably contacts the first terminal. In the present embodiment, the electrode 9 is combined with the electrode terminal 22 to configure an electrode device 24. In the present embodiment, the tip device 1 is combined with the electrode device 24 to configure a tip electrode set 25. FIG. 12 illustrates the state in which connection between the base connector 7a and the holder connector 7c is completed, and the electrode terminal 22 and holder terminal 23 are in contact with each other. FIG. 13 illustrates a state during the transition from the connected state to the disconnected state between the base connector 7a and the holder connector 7c, in which the electrode terminal 22 and the holder terminal 23 are disconnected from each other. The electrode terminal 22 and the holder terminal 23 are, for example, each formed from a metal such as silver.

The electrode device 24 may be distributed, sold, and stored together with or separately from the tip device 1 or the tip container set 3 (such as the one illustrated in FIG. 5 or FIG. 10).

The electrode terminal 22 includes a contact portion 22a arranged on the rear end face of the base 8 and a shaft 22b that connects the contact portion 22a to the electrode 9, but this configuration is not limiting. The contact portion 22a of the electrode terminal 22 is disc-shaped and centered on the axial center O, but this configuration is not limiting. The shaft 22b of the electrode terminal 22 is a cylindrical column centered on the axial center O, but this configuration is not limiting. The rear end of the electrode 9 is connected to the head of the shaft 22b, but this configuration is not limiting.

The holder terminal 23 includes a contact portion 23a arranged on the upper end face 10b of the recess 10a in the electrode holder 10 and a shaft 23b that is disposed within a recess communication hole 10e communicating with the recess 10a and is connected to the contact portion 23a, but this configuration is not limiting. The contact portion 23a of the holder terminal 23 is disc-shaped and centered on the axial center O, but this configuration is not limiting. The shaft 23b of the holder terminal 23 is a cylindrical column centered on the axial center O, but this configuration is not limiting. The recess communication hole 10e is formed by a cylindrical inner peripheral surface centered on the axial center O, but this configuration is not limiting.

The electrode device 24 is, for example, disposed in the tip device 1 after the liquid L is introduced into the tip 6 of the tip device 1.

With the electrode device 24 disposed in the tip device 1, the base connector 7a is connected to the holder connector 7c so that the contact portion 22a of the electrode terminal 22 and the contact portion 23a of the holder terminal 23 are sandwiched between the rear end face (upper end face) of the base 8 and the upper end face 10b of the recess 10a to be in contact with each other. This contact between the electrode terminal 22 and the holder terminal 23 enables the application of an electric field between the sample and the electrode 9.

Also, by the base connector 7a being disconnected from the holder connector 7c, the contact portion 22a of the electrode terminal 22 and the contact portion 23a of the holder terminal 23 can be detached from each other. Therefore, when the tip device 1 held in the electrode holder 10 is replaced, the electrode device 24 can also be replaced. Accordingly, liquid L that was attached to the electrode 9 before replacement of the tip device 1 can be prevented from mixing with the liquid L in the tip device 1 after the replacement. This effect is particularly noticeable in a case in which the tip devices 1 before and after replacement hold different types of liquid L from each other.

Other points regarding the measuring, injecting, collecting, and the like of samples such as cells using the tip electrode apparatus 5 of the present embodiment are the same as in the embodiment described above.

The above embodiment is an example of the present disclosure, and a variety of modifications may be made.

REFERENCE SIGNS LIST

1 Tip device
2 Container
3 Tip container set
4 Electrode apparatus
5 Tip electrode apparatus
6 Tip
6a Rear end of tip
6b Head of tip
6c Inner peripheral surface of tip
7a Base connector (first connector)
7b Container connector (second connector)
7c Holder connector (second connector)
8 Base
8a Outer peripheral surface of base
9 Electrode
10 Electrode holder
10a Recess 10b Upper end face of recess
10c Inner peripheral surface of recess
10d Head of electrode holder
10e Recess communication hole
11 Grip
12 Access hole
13 Guide face
14 Grounding portion
15 Communication hole
16 Cap
16a Tube wall
16b Flange
16c Inner peripheral surface of tube wall
17 Container body
17a Opening
17b Inner peripheral surface of opening
17c Torso
18 Sealed space
19 Blocking cap
20 First sealing member
21 Second sealing member
22 Electrode terminal (first terminal)
22a Contact portion
22b Shaft
23 Holder terminal (second terminal)
23a Contact portion
23b Shaft
24 Electrode device
25 Tip electrode set
O Axial center
S Surface
L Liquid

The invention claimed is:

1. A tip container set comprising:
an electrode;
an electrode holder;
a tubular tip;
a base that is continuous with a rear end of the tip and includes a first connector; and
a container configured to house a whole of the tip and including a second connector that detachably connects to the first connector,
wherein tip container set further comprises a first terminal continuous with a rear end of the electrode, and
wherein the electrode holder includes a second terminal that detachably contacts the first terminal.

2. The tip container set of claim 1, wherein the container includes a communication hole through which an exterior of the container communicates with the rear end of the tip.

3. The tip container set of claim 1, wherein the container includes a cap and a container body, the cap including the second connector, and the container body including an opening that detachably connects to the cap.

4. The tip container set of claim 1, wherein the base is located between the first connector and a head of the tip and includes a grip that is wider in a radial direction of the tip.

5. The tip container set of claim 1, wherein the base includes an access hole that communicates with the rear end of the tip.

6. The tip container set of claim 5, wherein the access hole includes a guide face that gradually narrows in diameter towards the rear end of the tip.

7. The tip container set of claim 1, wherein the base includes a grounding portion configured to maintain a head of the tip separated from a flat surface on which the tip is placed.

8. The tip container set of claim 7, wherein the grounding portion is located on an outer peripheral surface of the base.

9. The tip container set of claim 1, wherein the first connector and the second connector connect by concavo-convex engagement with each other.

10. The tip container set of claim 1, wherein the first connector and the second connector connect by screwing together.

11. A tip electrode apparatus comprising:
a tubular tip;
a base that is continuous with a rear end of the tip and includes a first connector;
an electrode holder including a second connector that detachably connects to the first connector; and
a linear electrode that protrudes from the electrode holder and is configured to be introduced into the rear end of the tip and terminate within the tip in the state in which the second connector connects to the first connector,
wherein tip electrode apparatus further comprises a first terminal continuous with a rear end of the electrode, and
wherein the electrode holder includes a second terminal that detachably contacts the first terminal.

12. The tip electrode apparatus of claim 11, wherein the base is located between the first connector and a head of the tip and includes a grip that is wider in a radial direction of the tip.

13. The tip electrode apparatus of claim 11, wherein the base includes an access hole that communicates with the rear end of the tip.

14. The tip electrode apparatus of claim 13, wherein the access hole includes a guide face that gradually narrows in diameter towards the rear end of the tip.

15. The tip electrode apparatus of claim 11, wherein the base includes a grounding portion configured to maintain a head of the tip separated from a flat surface on which the tip is placed.

16. The tip electrode apparatus of claim 15, wherein the grounding portion is located on an outer peripheral surface of the base.

17. The tip electrode apparatus of claim 11, wherein the first connector and the second connector connect by concavo-convex engagement with each other.

18. The tip electrode apparatus of claim 11, wherein the first connector and the second connector connect by screwing together.

19. A tip electrode set comprising:
a tubular tip;
a base that is continuous with a rear end of the tip and includes a first connector; and
an electrode device including a linear electrode configured to be introduced into the rear end of the tip and a first terminal continuous with a rear end of the electrode, the electrode terminating within the tip in the state in which the first terminal connects to the rear end face of the base, wherein
the first connector detachably connects to a second connector provided in an electrode holder, and
the first terminal detachably contacts a second terminal provided in the electrode holder.

* * * * *